(12) United States Patent
Luetke-Harmann et al.

(10) Patent No.: US 8,578,689 B2
(45) Date of Patent: Nov. 12, 2013

(54) FRONT ATTACHMENT FOR A SELF-PROPELLED COMBINE HARVESTER FOR HARVESTING STALKED CROP

(75) Inventors: Tim Luetke-Harmann, Sendenhorst (DE); Bernhard Aerdker, Warendorf (DE)

(73) Assignee: CLAAS Selbstfahrende Erntemaschinen GmbH, Harsewinkel (DE)

( * ) Notice: Subject to any disclaimer, the term of this patent is extended or adjusted under 35 U.S.C. 154(b) by 0 days.

(21) Appl. No.: 13/540,747

(22) Filed: Jul. 3, 2012

(65) Prior Publication Data

US 2013/0014483 A1 Jan. 17, 2013

(30) Foreign Application Priority Data

Jul. 12, 2011 (DE) .......................... 10 2011 051 792

(51) Int. Cl.
*A01D 45/02* (2006.01)
(52) U.S. Cl.
USPC ................................. 56/119; 56/51
(58) Field of Classification Search
USPC .................. 56/51, 52, 119, 53, 60, 92, 62
See application file for complete search history.

(56) References Cited

U.S. PATENT DOCUMENTS

| | | | | |
|---|---|---|---|---|
| 5,722,225 A * | 3/1998 | Wuebbels et al. | ................. | 56/60 |
| 5,845,472 A * | 12/1998 | Arnold | ................. | 56/94 |
| 5,852,922 A * | 12/1998 | Over Behrens et al. | ........ | 56/14.7 |
| 6,073,429 A * | 6/2000 | Wuebbels et al. | ............. | 56/11.3 |
| 6,119,443 A * | 9/2000 | Rauch | ................. | 56/64 |
| 6,298,643 B1 * | 10/2001 | Wuebbels et al. | ................. | 56/60 |
| 6,430,907 B2 * | 8/2002 | Wolters et al. | ..................... | 56/64 |
| 6,588,190 B2 * | 7/2003 | Steppat | ........................ | 56/119 |
| 6,658,832 B2 * | 12/2003 | Wubbels et al. | ................. | 56/94 |
| 6,701,702 B2 * | 3/2004 | Wubbels | ......................... | 56/103 |
| 6,775,967 B2 * | 8/2004 | Wubbels | ......................... | 56/60 |
| 6,782,682 B2 * | 8/2004 | Steppat | ........................ | 56/119 |
| 6,826,897 B2 * | 12/2004 | Wubbels | ......................... | 56/51 |
| 6,959,529 B2 * | 11/2005 | Wubbels | ......................... | 56/60 |
| 7,047,717 B1 | 5/2006 | Wolters et al. | | |
| 7,062,896 B2 * | 6/2006 | Resing et al. | ..................... | 56/64 |
| 7,062,897 B2 * | 6/2006 | Rickert et al. | .................. | 56/103 |
| 7,121,070 B2 * | 10/2006 | Krone et al. | ...................... | 56/62 |
| 7,222,478 B2 * | 5/2007 | Bruening et al. | ................. | 56/51 |
| 7,478,520 B2 * | 1/2009 | Rickert et al. | .................... | 56/51 |
| 7,571,592 B2 * | 8/2009 | Rickert et al. | .................... | 56/51 |
| 7,578,118 B2 * | 8/2009 | Rickert et al. | .................. | 56/119 |
| 7,905,078 B2 * | 3/2011 | Rickert et al. | .................... | 56/53 |

(Continued)

FOREIGN PATENT DOCUMENTS

| | | |
|---|---|---|
| DE | 10 2005 021 792 | 11/2006 |
| DE | 10 2009 051 053 | 12/2010 |
| EP | 1 106 049 | 6/2001 |

*Primary Examiner* — Árpád Fábián-Kovács
(74) *Attorney, Agent, or Firm* — Michael J. Striker

(57) ABSTRACT

A front attachment for a self-propelled combine harvester includes intake conveyor mechanisms arranged side by side having grooved conveyor wheels that rotate about a vertical rotational axis. Snapping units located downstream of the intake conveyor mechanisms in the direction of crop flow have snapping rollers extending horizontally and transversely to the direction of travel. A transverse conveyor is equipped with opposing auger sections drawn together in the center of the front attachment. The grooved conveyor wheels include extending driving elements that engage via sections thereof into guide channels to pick up and convey plant stalks in the direction of the center of the front attachment.

21 Claims, 4 Drawing Sheets

(56) References Cited

U.S. PATENT DOCUMENTS

| | | |
|---|---|---|
| 8,104,254 B2 | 1/2012 | Luetke-Harmann et al. |
| 2003/0079457 A1* | 5/2003 | Wubbels .......................... 56/52 |
| 2003/0101703 A1* | 6/2003 | Wubbels .......................... 56/51 |
| 2004/0123576 A1* | 7/2004 | Bruening ......................... 56/51 |
| 2005/0132688 A1* | 6/2005 | Resing ............................. 56/51 |

* cited by examiner

FRONT ATTACHMENT FOR A SELF-PROPELLED COMBINE HARVESTER FOR HARVESTING STALKED CROP

CROSS-REFERENCE TO A RELATED APPLICATION

The invention described and claimed hereinbelow is also described in German Patent Application DE 10 2011 051 792.8 filed on Jul. 12, 2011. This German Patent Application, subject matter of which is incorporated herein by reference, provides the basis for a claim of priority of invention under 35 U.S.C. 119(a)-(d).

BACKGROUND OF THE INVENTION

The invention relates to a front attachment for a self-propelled combine harvester for harvesting stalked crop such as corn or sunflowers. The front attachment comprises a plurality of intake conveyor mechanisms arranged side by side and each comprising grooved conveyor wheels that rotate about a substantially vertical rotational axis. The front attachment further comprises snapping units located downstream of the intake conveyor mechanisms in the direction of crop flow that comprise snapping rollers extending horizontally and transversely to the direction of travel and, a transverse conveyor. The transverse conveyer is equipped with opposing auger sections, via which harvested corn cobs or fruits from sunflowers are drawn together in the center of the front attachment and fed from there to a feed rake. The grooved conveyor wheels of the individual intake conveyor mechanisms comprise, on the outer circumference thereof, radially extending driving elements, which engage via sections thereof into guide channels to pick up and convey corn plants or sunflowers. The guide channels are oriented substantially in the direction of travel in the inlet region thereof and, in the outlet region thereof, in the direction of a snapping gap formed between the snapping rollers.

Corn is cultivated in rows separated by substantially constant distances, wherein sowing is carried out by sowing individual seeds, and the corn plants that have gone to seed reach a height of up to three meters. The corn plant substantially comprises a corn stalk, corn leaves having a length of up to one meter, and fruits in the form of corn cobs enclosed by husks. There are two main types of corn harvesting, namely, harvesting using a corn harvester to fragmentize the entire corn plant, including the corn kernels, to permit the subsequent use thereof as feed, in the form of corn for silage. In fragmentized form, the corn plant also can be supplied as biomass to biogas plants. The corn harvesters used to harvest the corn plants process the entire corn plant, as explained previously, and therefore the fruit (that is, the corn cobs comprising the corn kernels), do not need to be removed from the remaining plant components.

In contrast, a combine harvester is used to harvest grain corn that is typically equipped with a front attachment for harvesting corn or sunflowers instead of the usual header thereof that is used to harvest grain. The front attachment ensures that the entire plant is drawn in a controlled manner into a snapping unit in which the fruits are removed from the stalks of the plant and are subsequently fed by way of a feed rake to a threshing mechanism of the combine harvester.

There are front attachments that are suited exclusively to harvesting the corn plants in a row-dependent manner. Therein, individual intake conveyor mechanisms must be adjusted according to the distance between the rows, and the combine harvester must be operated with the front attachment oriented according to the rows. Various attempts to develop a row-independent harvesting procedure in which the harvesting machine does not need to follow the row crop exactly are known. Such known processes, however, are fraught with considerable problems because it must be ensured that the corn plants that are not located in a row extending continuously with respect to the particular intake conveyor mechanism are captured by same and are subsequently fed to the downstream snapping units.

A front attachment for a combine harvester that is provided for harvesting grain corn is known from DE 10 2009 051 053 A1. Distributed along the width thereof is a plurality of intake conveyor mechanisms, which form guide channels and are separated from one another. Each of the intake conveyor mechanisms comprises a plurality of rotating grooved conveyor wheels, which are disposed on substantially vertical rotational axes, capture the corn plant at the corn stalk thereof and subsequently transport them through the particular guide channel. Different groups of intake conveyor mechanisms having different arrangements of the grooved conveyor wheels also are provided. An intake conveyor mechanism disposed in the center of the front attachment and intake conveyor mechanisms positioned on both sides thereof work together. The intake conveyor mechanisms capture the corn plants and convey them through the two guide channels in the end sections thereof, which point outwardly relative to the center intake conveyor mechanism and the center of the front attachment.

In the known front attachment, only four crop inlet openings are provided and, instead of the individual, outwardly located grooved conveyor wheels, intake conveyor mechanisms that correspond to the design of the centrally located intake conveyor mechanism are required to increase the working width of the front attachment. In this case as well, the crop flow would be conveyed outwardly once more by the guide channels formed as a result, in the end section thereof.

A similar arrangement of intake conveyor mechanisms of a front attachment for harvesting grain corn is known from DE 10 2005 021 792 A1. In that case, however, each of the intake conveyor mechanisms comprises two grooved conveyor wheels, which are driven in opposite directions. The intake conveyor mechanisms disposed on both sides of a longitudinal central plane likewise ensure that the corn plants fed into the center are transported toward the outside.

Furthermore, EP 1 106 049 A1 discloses a front attachment designed to permit harvesting to be carried out in a row-independent manner. In that case, each of the intake conveyor mechanisms are driven in the same direction and have upper and lower tine rotors that are curved in different directions in the end regions thereof. A snapping unit, which extends in the direction of travel, is disposed next to each of the tine rotors, from the snapping plates thereof outward the harvested corn cobs are fed to a downstream transverse conveyor. The corn stalks and the corn leaves that are drawn through the snapping gap reach a chopper, which is located underneath the snapping plates, fragmentizes the components and deposits them onto the field.

SUMMARY OF THE INVENTION

The present invention overcomes the shortcomings of known arts, such as those mentioned above, to process the most continuous crop flow possible and achieving high crop throughput.

The invention provides a harvesting device comprising a front attachment designed for harvesting grain corn in a row-dependent manner, with the same advantages. During the snapping procedure, the stalk of the plant is pulled in the direction of the ground and, during the motion, is fragmentized and deposited on the field via a chopping device. Moreover, it also is possible to provide a mulching device underneath the feed rake of the combine harvester or to mount the mulching device on the rear end of the combine harvester. For that matter, the corn straw comprising the corn stalks and the leaf portions also can be fragmentized in a subsequent separate processing step using a device that is driven by a tractor, allowing such corn straw to be better worked into the ground and distributed therein.

In an embodiment, the invention provides a front attachment configured in a way that an optimal flow of the stalked plants can take place through the individual intake conveyor mechanisms and the snapping units located downstream thereof, assuring that fruits removed from the plant can be guided away in an optimal manner. The structural dimensions of the front attachment should not be increased compared to known solutions and should even be reduced if necessary, to accommodate use on existing agricultural machines.

The inventive front attachment includes guide channels equipped with end sections that guide the stalked crop in the direction of the center of the front attachment. By steering the crop in a targeted manner, the fruits removed from the plant are carried away in an optimized manner. The occurrence of blockage in the crop flow is reduced in this manner.

In greater detail, a central intake conveyor mechanism disposed in the center of the front attachment is equipped with guide channels extending on both sides thereof, the end sections of which (that guide the plants into the snapping unit), are oriented in the direction toward the center of the front attachment or in the conveyance direction of the transverse conveyor. The snapping unit assigned to the central intake conveyor mechanism is disposed in the region of the central intake conveyor mechanism facing away from the direction of travel. A result thereof is a material flow in the last section, as viewed in the direction of flow, of the guide channels, which delimit the central intake conveyor mechanism, and in the snapping unit directly downstream thereof, which is the same as the conveyance direction of the transverse conveyor in both cases.

The transverse conveyor, which is designed as an auger, has opposing auger flights and draws the crop, namely the fruits, transferred thereupon together toward the center of the front attachment. An intake opening is disposed in the center of the front attachment, via which the fruits are fed to a feed rake, in the form of a chain conveyor. As a result, the crop flow is substantially improved in that a redirection, that is, a substantial change in the direction of motion of the conveyed fruits, is prevented. The fruits move in the end section of the two guide channels and in the snapping units together with the remainder of the plant and, separated therefrom, subsequently above a snapping gap always in the conveyance direction of the transverse conveyor.

In contrast, according to documents DE 10 2009 051 053 A1 and DE 10 2005 021 792 A1, material is forced to flow outwardly at least for the intake conveyor mechanism provided for the center of the front attachment. According, the particular auger section of the transverse conveyor then captures the corn cob and forces it to change the direction of motion thereof. The same applies substantially for the front attachment according to EP 1 106 049 A1 because therein, a motion of the corn cob is induced, overall, by only one part of the rotor, the motion matching the direction of motion of the transverse conveyor. As this front attachment comprises six intake regions and rotors, the corn cobs are transported from half of all the rotors against the conveyance direction of the transverse conveyor.

According to the invention, in contrast, all inner and outer intake conveyor mechanisms, in addition to the central intake conveyor mechanism, are equipped with guide channels, the end sections of which are oriented in the direction of the center of the front attachment or in the conveyance direction of the transverse conveyor. The end sections lead into snapping units, which are located spatially behind the particular further snapping unit. When intake conveyor mechanisms that have an identical design or different designs are arranged side by side, a guide channel is therefore formed between each one, which, together with the downstream snapping unit, is always oriented toward the center of the front attachment and, therefore, toward the center of the combine harvester. This provides for a material flow at these further end sections of guide channels as well that has the same direction as the material flow generated by the transverse conveyor.

An embodiment of the central intake conveyor mechanism that is advantageous overall and a favorable conveyance effect can be furthermore achieved by equipping it with four rotating grooved conveyor wheels, the rotational axes of which are located with respect to one another on an isosceles trapezoid. Preferably, one short leg of the trapezoid extends in the direction of travel and the long leg of which extends in the direction of the transverse conveyor. A divider is typically disposed on an axis of symmetry of the central intake conveyor mechanism, which is therefore disposed upstream of the shorter leg of said isosceles trapezoid. The front grooved conveyor wheels capture the plant stalks in the intake region of the central intake conveyor mechanism and move them, together with grooved conveyor wheels of the adjacent inner intake conveyor mechanisms, into the particular guide channel. The two rear grooved conveyor wheels redirect the conveyed flow into a transverse direction, that is, in the direction toward the center of the central intake conveyor mechanism. This geometric configuration of the arrangement of the grooved conveyor wheels makes it possible to obtain a very compact design of the central intake conveyor mechanism, and makes it possible, as will be described further in the following, to achieve a system design to expand the front attachment with additional units of inner intake conveyor mechanisms. The result is a modular system that is low-cost and suitable for series production.

Moreover, the two pair of snapping rollers are assigned to the central intake conveyor mechanism, the rear, as viewed in the direction of travel, snapping roller of which is axially extended and comprises, in the region of the axial extension thereof, an intake auger engages by way of a portion of the outer jacket thereof into the end section of the guide channel. Since the plant stalk is pressed into the rear edge region of the end section by the grooved conveyor wheel that conveys the particular plant stalk into the curved end section of the guide channel that extends transversely to the direction of travel, the end of the rear snapping roller that is extended by the intake auger tangentially adjoins same. The intake auger then draws the stalk into the snapping gap, thereby supporting the material flow at this point in a corresponding manner. The pair of snapping rollers, that is, the front snapping roller and the rear snapping roller, are preferably coaxially arranged. Furthermore, it also is possible to locate the pair of snapping rollers and, therefore, the two snapping gaps with slight offset with respect to one another in the horizontal direction. If space for housing the two snapping devices becomes a problem, they also can be extended or offset relative to one another in such a way that they overlap in the axial extension thereof.

A structurally favorable embodiment of the guide channels and the snapping units results in that the guide channels are formed via lower and upper covers of the grooved conveyor wheels. The covers comprise appropriately configured edge regions that assume the guidance of the plant stalks and extend, in sections, in front of the grooved conveyor wheels used to convey the plants. Since the lower cover simultaneously forms the front snapping plate, the corresponding guide channel transitions directly into the snapping gap that extends transversely to the direction of travel, thereby allowing the plant stalks to enter, unobstructed, the snapping gap that is formed together with a rear snapping plate.

As explained above, the plant stalks, which still comprise the fruits, are moved into the corresponding snapping unit on the outer jacket of the central intake conveyor mechanism within the corresponding guide channels. The fruits that separate from the plant stalk by the plant stalk being drawn downward through the snapping gap reach the rear and front snapping plates. In this phase, the fruits that are separated from the plant are moved toward one another and must make a motion in the direction of the auger flights provided on the transverse conveyor. A deflector, which directs the fruits in the appropriate direction, is provided for this purpose. The deflector preferably comprises a tip that points in the direction of the transverse conveyor, that is, it is a component having an approximately triangular contour. The corresponding legs of the deflector, which preferably has a triangular contour, are provided with guide radii. The deflector however, may alternatively have a different geometric shape suitable for directing the fruits in the direction of the transverse conveyor. Moreover, it is advantageous to use the region of the deflector to provide a supporting rail there, by way of which the central intake conveyor mechanism, that is, the front snapping plate with the grooved conveyor wheels mounted thereon, is fixed on the front attachment. It also is possible to form the appropriate deflector directly on the lower cover, that is, on the front snapping plate. Simple and relatively low-cost embodiments are achieved overall as a result.

To improve the material flow and create a compact design of the front attachment, the snapping unit is shifted relatively far rearward in every case, that is, for the central intake conveyor mechanism and the other intake conveyor mechanisms. The snapping gap is therefore located behind an imaginary line defined by projecting the outer extension of the auger of the transverse conveyor onto the snapping plates.

A low-cost arrangement is made possible in that the rear snapping plate simultaneously forms a portion of a trough of the front attachment. In one form, the rear snapping plate is axially displaceable, thereby allowing the width of the snapping gap to be adjusted by way of an appropriate adjustment device. The adjustment can be carried out using hydraulic, mechanical or electrical actuators.

According to a further embodiment of the invention, the inner intake conveyor mechanisms disposed on both sides of the central intake conveyor mechanisms each have a substantially rhomboidal outer contour and mirror symmetry with respect to a longitudinal central plane of the front attachment and can be arranged side by side in any manner. The result is a modular system in which two embodiments of the inner intake conveyor mechanisms exist that are substantially identical but are mirror images of one another. The inner intake conveyor mechanisms convey the corn or sunflower plant in the direction of the center of the front attachment. The sides of the rhomboidal inner intake conveyor mechanisms are adapted to the above-described trapezoidal shape of the central intake conveyor mechanism in such a way that the relevant guide channels are produced. The ultimate result is that, in addition to an appropriate design of a central intake conveyor mechanism, only two mirror-image variants are required for the further intake conveyor mechanisms. As such, manufacturing costs and stocking costs are considerably reduced overall.

The potential throughput of crop can be increased for the further intake conveyor mechanisms and the snapping units connected thereto by extending the relevant snapping rollers on said units. In contrast to the central intake conveyor mechanism, in which the crop flows on both sides are moved toward one another and through the snapping units (thereby limiting the space available for placement of both pair of snapping units), the snapping rollers of the other units can be formed across the entire length thereof. A deflector that extends in the direction of the transverse conveyor also is provided at the snapping gap provided at the units. The deflector directs the fruits removed from the plant stalks into the intake region of the spiral-shaped transverse conveyor.

Further features according to the invention relate to the design of the grooved conveyor wheels. The grooved conveyor wheels are equipped with teeth, which are formed with a radius at the tooth flanks and the tooth roots thereof. The radius can either be matched to the standard stalk diameter of the plants or is designed such that the stalk is transported without being bent. One of the tooth flanks of each of the teeth extends at an angle with the longitudinal central axis of the corresponding grooved conveyor wheel. The slant of the tooth flank causes the plant to slant accordingly during transport thereof, and so the end of the corn or sunflower plant containing the fruit is brought into a favorable slanted position that reduces a possible loss of fruits during the snapping procedure.

It is further advantageous to widen the tooth flanks that come in contact with the plant stalk to allow the plant stalk to be transported in a relatively gentle manner, without being bent whatsoever. This is accomplished by providing an appropriate transition from the tooth flank into an end face of the grooved conveyor wheel having a transition radius or a chamfer, that is, a broken edge.

Preferably, the grooved conveyor wheels should be manufactured using means that are favorable in terms of production engineering, thereby resulting in considerable advantages for series production. For instance, each of the grooved conveyor wheels can be made of plastic, and/or to produce the grooved conveyor wheels from sheet metal in a non-material-removing forming process.

BRIEF DESCRIPTION OF THE DRAWINGS

Further features and advantages of the invention will become apparent from the description of embodiments that follows, with reference to the attached figures, wherein.

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1:
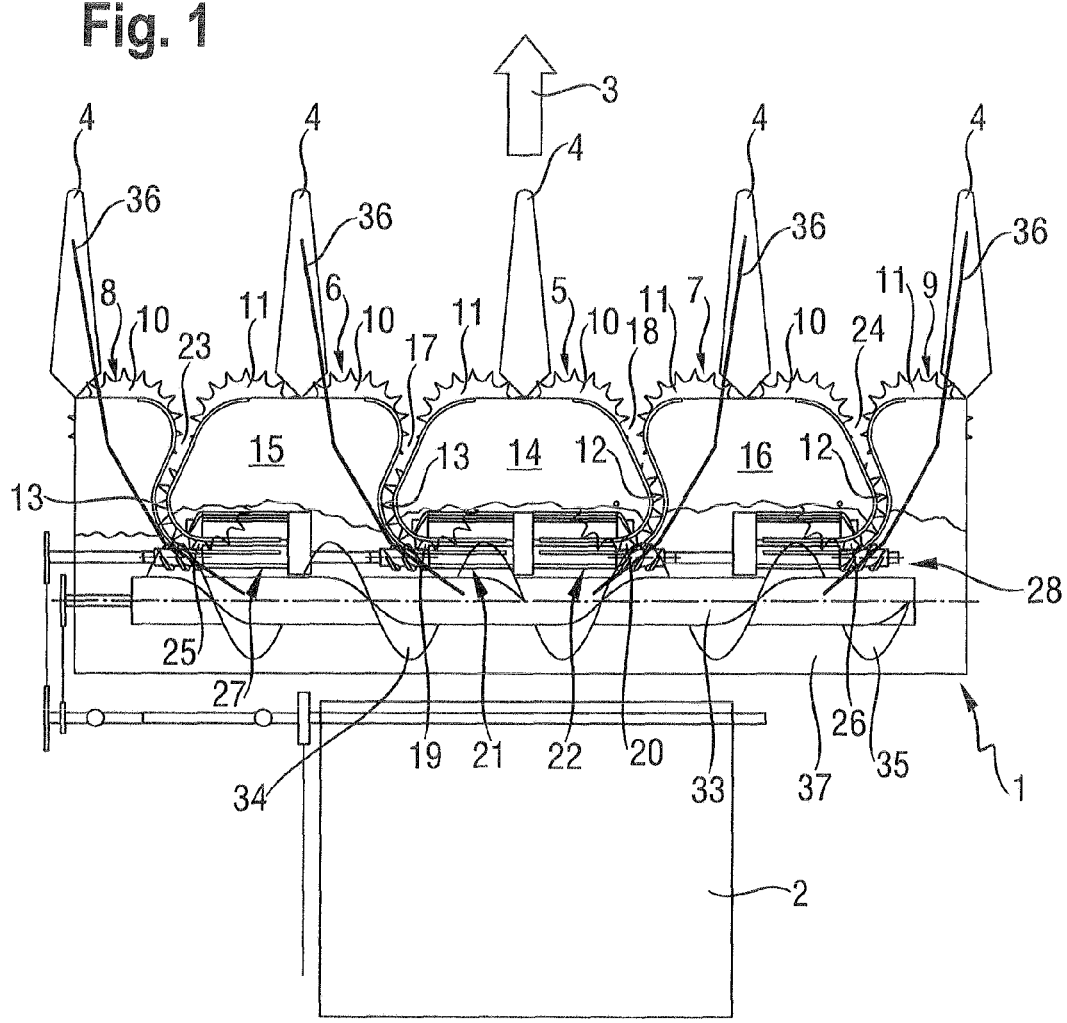
FIG. 1 is a schematic top view of a front attachment according to the invention, including a sectional detail view in the region of snapping units, wherein the front attachment is connected to a feed rake of a combine harvester and comprises a plurality of intake conveyor mechanisms.

In FIG. 1, reference character 1 labels a front attachment for harvesting grain corn that is coupled to a feed rake 2 of a self-propelled combine harvester (which is not shown in greater detail). The feed rake 2 is used to feed the crop, e.g., corn cobs, to a not-shown threshing mechanism of the combine harvester. The corn kernels are thereby removed from the cobs during the threshing process. During the harvesting process, the front attachment 1 is operated in a direction of travel indicated by an arrow 3.

In the front region thereof, the front attachment 1 comprises a total of five dividers 4, each of which is assigned to a downstream intake conveyor mechanism. A first, central intake conveyor mechanism 5 is provided in the center of the front attachment 1, which has a substantially trapezoidal outer contour. Central intake conveyor mechanism 5 interacts with a first inner intake conveyor mechanism 6 and a second inner intake conveyor mechanism 7, which are disposed on both sides of the central intake conveyor mechanism 5. The first inner intake conveyor mechanism 6 and the second inner intake conveyor mechanism 7 have a substantially rhomboidal outer contour, that is, the basic shape of a parallelogram. As such, mechanisms 6, 7 are designed as mirror images of one another. Outer intake conveyor mechanisms 8 and 9 are provided as terminations at the two outer ends of the front attachment 1. The function of outer intake conveyor mechanisms 8 and 9 corresponds to that of the inner intake conveyor mechanisms 6 and 7 (to be described in greater detail below. Each of the intake conveyor mechanisms 5 to 7 disposed between the outer intake conveyor mechanisms 8 and 9 comprises first grooved conveyor wheels 10 in the front region thereof. Each first grooved conveyor wheel rotates in the clockwise direction and is engaged with second grooved conveyor wheels 11 rotating in the counterclockwise direction.

Figure 2:
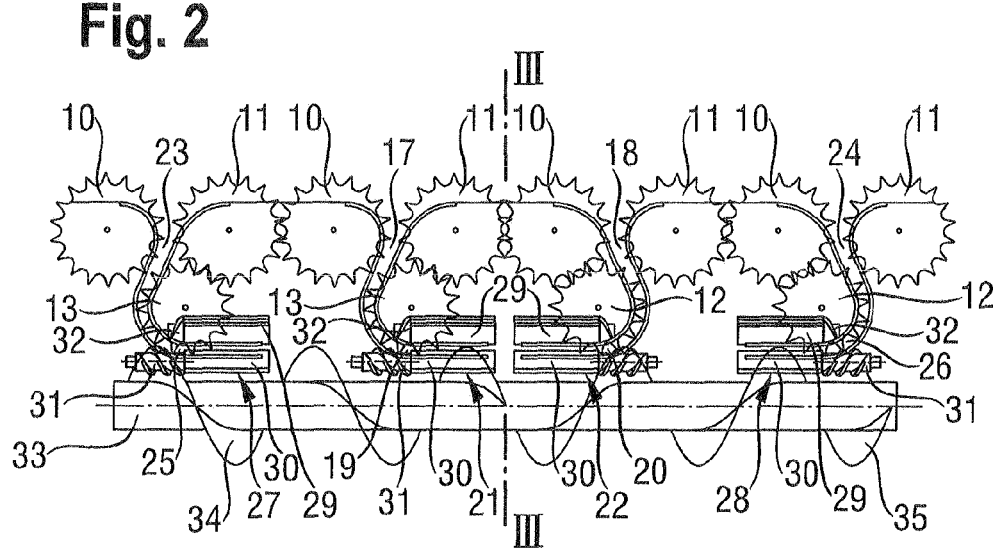
FIG. 2 is another schematic top view of the front attachment shown in FIG. 1, in which top covers have been removed to show details of the intake conveyor mechanisms.

As shown in FIG. 1 in combination with FIG. 2, the central and inner intake conveyor mechanisms 5 to 7 comprise third grooved conveyor wheels 12 that rotate in the clockwise direction and/or fourth grooved conveyor wheels 13 that rotate in the counterclockwise direction, each of which is used to redirect the material flow. The front attachment 1 can harvest the plants in a row-dependent manner or in a row-independent manner. In the row-independent manner, the plants may not be fed in an ordered manner. In addition, it is assumed that more than one row of plants is harvested with a front attachment 1 that operates in a row-independent manner (as depicted in FIG. 1).

The central intake conveyor mechanism 5 disposed in the center of the front attachment 1 comprises a top cover 14, which, together with top covers 15 and 16 of the inner intake conveyor mechanisms 6 and 7, form a first guide channel 17. The first guide channel 17 extends to the left of the central intake conveyor mechanism as viewed in the direction of travel 3, and a second guide channel 18 extending on the right. Covers 14, 15 and 16 are preferably produced as sheet metal or plastic elements and comprise an edge that is beaded or is reinforced in another manner and forms the guide channels 17, 18, 23 and 24 in the upper region thereof. In addition, the first grooved conveyor wheel 10 of the first inner intake conveyor mechanism 6 and the second grooved conveyor wheel 11 of the first intake conveyor mechanism 5 protrude into the first guide channel 17, The grooved conveyor wheels 10 and 11 capture the stalks of the particular plant in the front region of the first guide channel 17 and move it therein until the plant stalk is captured by the fourth grooved conveyor wheel 13 of the central intake conveyor mechanism 5 and is redirected into the transverse direction of the front attachment 1.

The plant is guided in the second guide channel 18 in a similar manner, assisted by the first grooved conveyor wheel 10 of the central intake conveyor mechanism 5 and the second grooved conveyor wheel 11 of the second inner intake conveyor mechanism 7. In this case, the material flow is redirected by the third grooved conveyor wheel 12 of the central intake conveyor mechanism 5. Directly following the redirection, the guide channels 17 and 18 comprise end sections 19 and 20, which extend in the transverse direction of the front attachment 1 and toward one another (see FIG. 2). The first end section 19 thus leads into a first snapping unit 21, while the second end section 20 leads in the opposite direction into a second snapping unit 22.

Further guide channels 23 and 24 are formed between the first inner intake conveyor mechanism 6 and the outer intake conveyor mechanism 8 adjacent thereto, and the second inner intake conveyor mechanism 7 and the outer intake conveyor mechanism 9 adjacent thereto. The guide channel 23 transitions into an end section 25 and the guide channel 24 transitions into an end section 26. Snapping units 27 and 28 are assigned to the end sections 25 and 26. FIG. 2 also shows that said end sections 25 and 26 and the subsequent snapping units 27 and 28 are likewise oriented in the direction toward the center of the front attachment 1. The snapping units 21, 22, 27 and 28 depicted in FIG. 2 essentially have the same configuration and comprise snapping rollers 29 and 30, which are driven in pairs. Each pair of snapping rollers comprises a front snapping roller 29 and a rear snapping roller 30, wherein each rear snapping roller 30 is axially extended and is equipped with an intake auger 31. By comparison, the various front snapping rollers 29 are shorter and are therefore equipped with a relatively short intake auger 32.

In addition, the snapping rollers 29 and 30 are profiled on the outer circumference thereof, in order to transport the plant stalk underneath the front attachment 1 during the snapping process. From underneath the front attachment 1, the plant stalk is fed to a not-shown chopping mechanism or is deposited onto the field. In the latter case, a mulching device can be disposed underneath the feed rake or behind the combine harvester, which fragmentizes the stalks and the leaf portions of the plant in such a way that they can rot in the ground after the final soil management process.

The snapping units 21, 22, 27 and 28 are adjoined by an auger-shaped transverse conveyor 33, which comprises opposing auger flights 34 and 35. When the transverse conveyor is driven, the auger flights 34 and 35 (which turn toward the left or the right), draw the fruits transported by the snapping units 21, 22, 27 and 28 into the intake region of the transverse conveyor 33 in the direction of the center of the front attachment 1. Consequently, the fruits enter the feed rake 2 via an inlet opening, which is not shown. In addition, guide frame members 36 are disposed on each of the outwardly located intake conveyor mechanisms 6, 7, 8 and 9, which extend from the dividers 4 thereof and into the region of the corresponding snapping units 21, 22, 27 and 28. By way of the guide frame members 36, the relatively long plant is guided in the upper region thereof, and is therefore reliably guided through the guide channels 17, 18, 23 and 24 in an upright position to the snapping units 21, 22, 27 or 28.

Further details of the device of FIGS. 1 and 2, are shown in FIGS. 3 to 8, as now will be explained.

Figure 3:
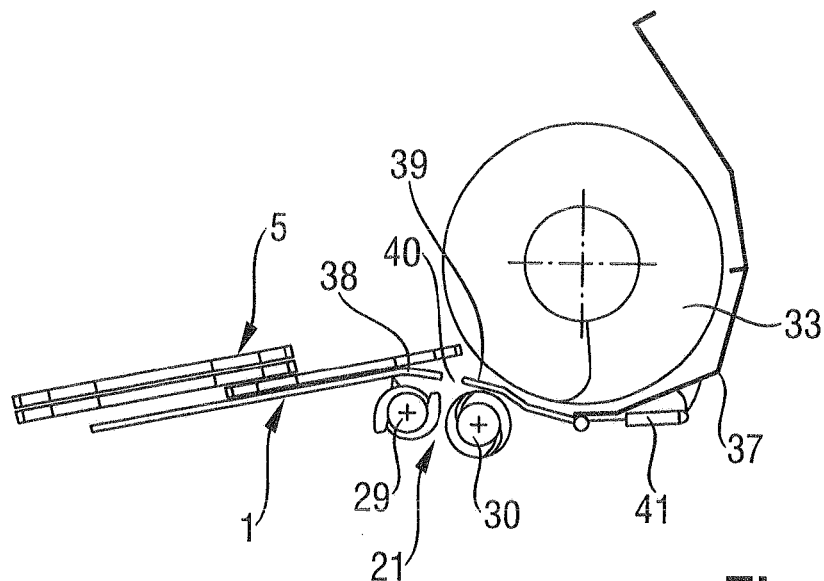
FIG. 3 presents a cross-sectional view of a central intake conveyor mechanism, a snapping unit disposed downstream thereof, and a transverse conveyor according to line in FIG. 2.

FIG. 3 shows, in a schematic sectional drawing, the arrangement of the central intake conveyor mechanism 5 in a front attachment 1 according to the invention. The transverse conveyor 33 is disposed in a header trough 37. It should be clear that the snapping unit 21 is disposed, by way of the front and rear snapping rollers 29 and 30, respectively, substantially within the radial extension of the transverse conveyor. A front snapping plate 38 and a rear snapping plate 39 are located above the snapping rollers 29 and 30. The snapping plates 38 and 39 delimit a snapping gap 40, by way of which the plant stalks are drawn in between the snapping rollers 29 and 30. The fruits are thus separated from the plant stalk via the corresponding snapping plates 38 and 39, where the plant stalk is drawn downward. It should be clear that the front snapping plate 38 simultaneously forms a lower cover of the central intake conveyor mechanism 5, while the rear snapping plate 39 extends to the header trough 37. An adjustment device 41 is located at the header trough 37, which engages at the rear snapping plate 39 and can displace the rear snapping plate in the longitudinal direction to change the snapping gap 40.

Figure 4:
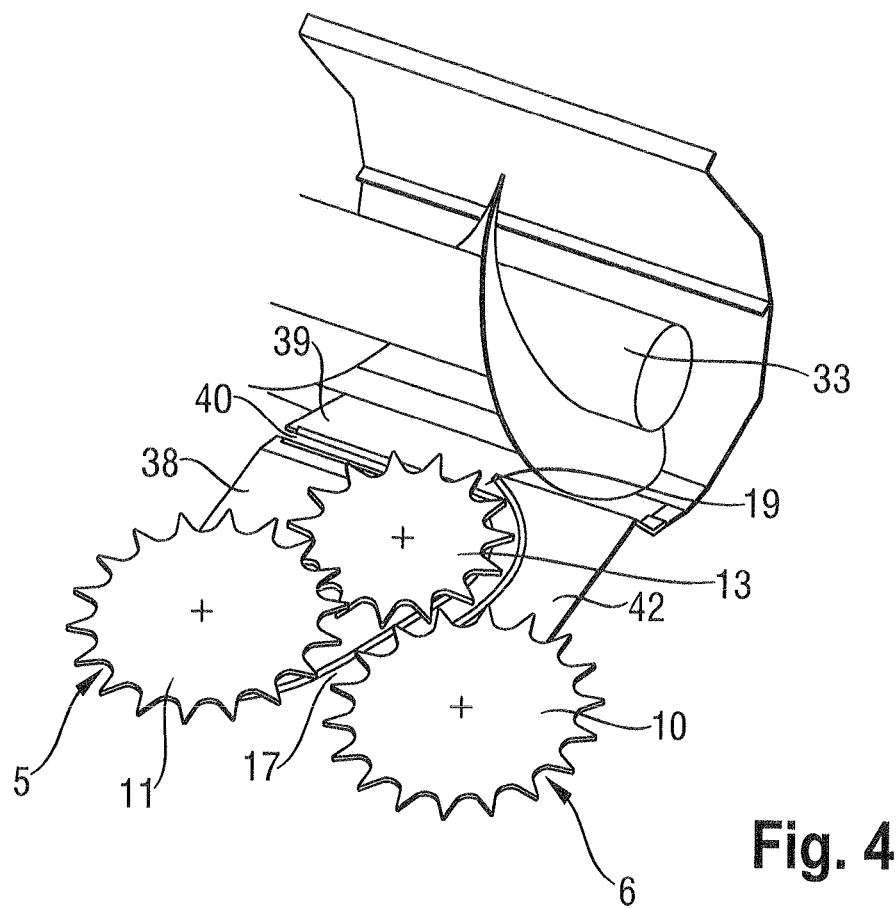
FIG. 4 presents a detailed view in the region of a feeder housing formed between the central intake conveyor mechanism and a further intake conveyor mechanism.

The corresponding arrangement of the two snapping plates 38 and 39 also is shown in FIG. 4, where the first guide channel 17, is located between the central intake conveyor mechanism 5 and the first inner intake conveyor mechanism 6, also is depicted. It should be clear that, on the front snapping plate 38, the second grooved conveyor wheel 11 is disposed in the front region and a fourth grooved conveyor wheel 13 is disposed in the rear region. The first grooved conveyor wheel 10 is disposed on a lower cover 42 of the adjacent first inner intake conveyor mechanism 6 and the two grooved conveyor wheels 10 and 11 draw the plants into the first guide channel 17. The first guide channel 17 then transitions at the end section 19 thereof into the snapping gap 40.

Figure 5:
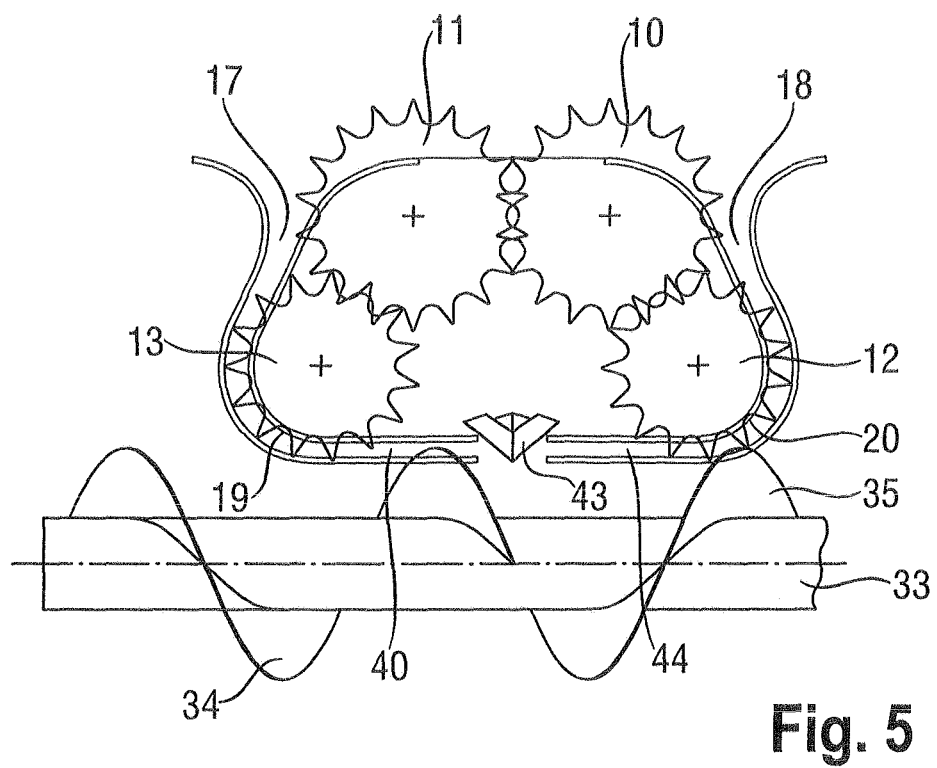
FIG. 5 presents a detailed view of the central intake conveyor mechanism comprising a deflector, which is disposed between end sections of guide channels thereof.

FIG. 5 presents an enlarged view of the central intake conveyor mechanism 5 that was described above with reference to FIG. 2, wherein a deflector 43 pointing in the direction of the transverse conveyor 33 also is provided. In the FIG. 5 embodiment, a further snapping gap 44 is located opposite the above-described snapping gap 40. Snapping gap 44 is connected to the second guide channel 18. The deflector 43 separates the two snapping gaps 40 and 44 from each other and ensures that the fruits picked from the plant are reliably fed to the auger flight 34 or 35 of the transverse conveyor 33, which convey in the same direction.

Figure 6:
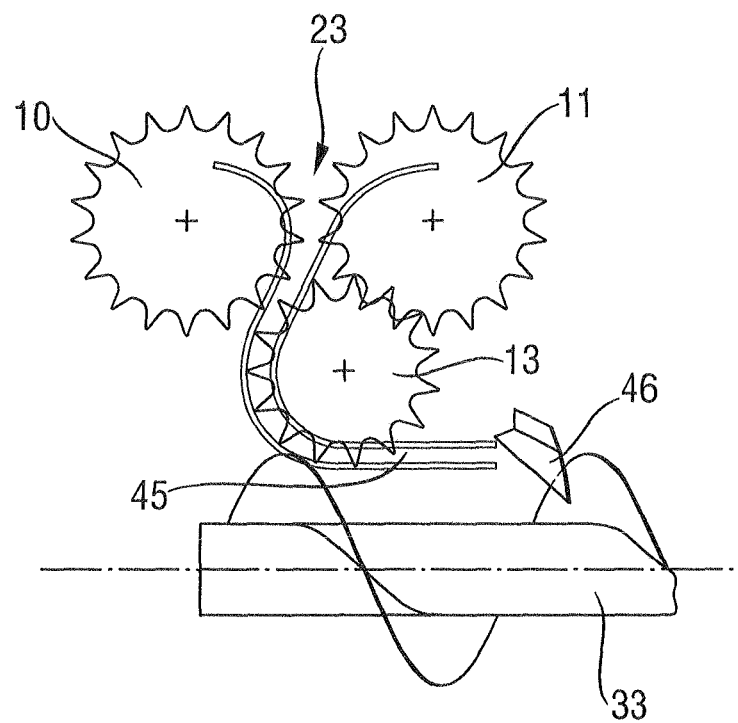
FIG. 6 presents a detailed view in the region of a guide channel formed between further intake conveyor mechanisms.

In a similar manner, as shown in FIG. 6, a further deflector 46 is assigned to the guide channel 23 and a snapping gap 45 adjacent thereto, which likewise directs the fruits in the direction of the transverse conveyor 33.

Figure 7:
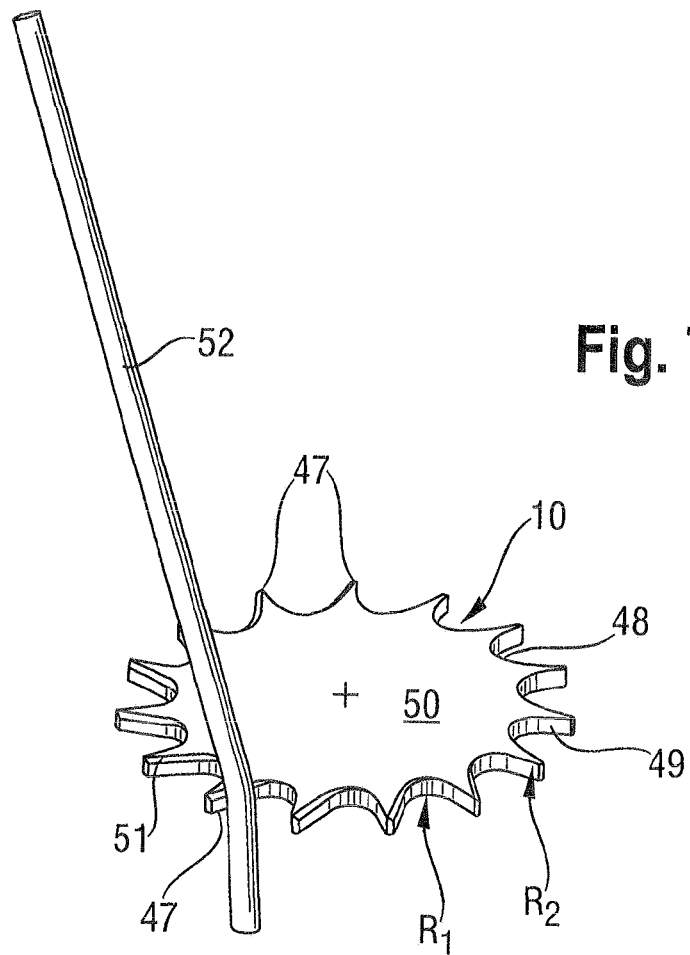
FIG. 7 presents a perspective depiction of a grooved conveyor wheel acting on a corn stalk.

FIGS. 7 and 9 show the embodiment of one of the grooved conveyor wheels 10, 11, 12, 13. FIG. 7 shows that a corresponding conveyor element (e.g., used as a first grooved conveyor wheel 10) comprises driving elements 47 in the form of teeth. Each driving element, which is in the form of a tooth, is provided with a first radius $R_1$ in the region of the tooth root 48 thereof and with a radius $R_2$ in the region of the tooth flank 49 thereof. As a result, the tooth flank 49 is substantially in the form of involute toothing. Moreover, FIG. 7 shows that the particular tooth flank 49 is rounded in the transition thereof onto an end face 50 of the grooved conveyor wheel 10 or is equipped with a bevel 51 or a chamfer. The purpose thereof is to prevent the plant stalk from possibly being bent to an extreme extent, which would cause the fruits to become lost before the entire plant can be fed to the snapping unit 21, 22, 27 or 28. FIG. 7 illustrates the function of the first grooved conveyor wheel 10, in which a plant stalk 52 is carried by the toothing.

Figure 8:
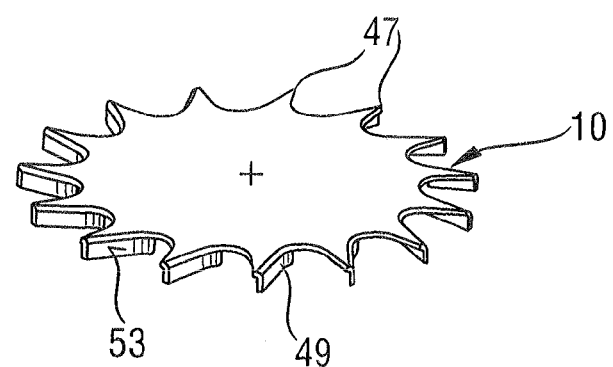
FIG. 8 a perspective view of a further embodiment of a grooved conveyor wheel as a single component.

According to FIG. 8, widened contact surfaces 53 are formed on the tooth flanks 49, which carry the plant stalk along due to the rotational direction of the grooved conveyor wheel 10. The widened contact surfaces likewise ensure that the plant stalk is transported in a gentle manner, that is, without being bent.

As shown in the aforementioned figures, the present invention provides that the material flow fed from one of the intake conveyor mechanisms 5 to 9 and downstream picking units 21, 22, 27 or 28 to the transverse conveyor 33 is transported in a direction that corresponds to the conveyance direction of the transverse conveyor 33. The crop flow is improved considerably as a result, and disruptions of snapping devices that operate in a row-independent manner in particular are prevented.

The following list of reference signs of various elements mentioned above is included (as follows), for ease of explanation:

LIST OF REFERENCE CHARACTERS 1 front attachment
2 feed rake
3 arrow for direction of travel
4 divider
5 central intake conveyor mechanism
6 inner intake conveyor mechanism
7 inner intake conveyor mechanism
8 outer intake conveyor mechanism
9 outer intake conveyor mechanism
10 first grooved conveyor wheel, conveying in the clockwise direction
11 second grooved conveyor wheel, conveying in the counterclockwise direction
12 third grooved conveyor wheel, conveying in the clockwise direction
13 fourth grooved conveyor wheel, conveying in the counterclockwise direction
14 top cover of 5
15 top cover of 6
16 top cover of 7
17 first guide channel, left
18 second guide channel, right
19 end section of 17
20 end section of 18
21 first snapping unit
22 second snapping unit
23 guide channel
24 guide channel 25 end section of 23
26 end section of 24
27 napping unit
28 snapping unit
29 front snapping roller
30 rear snapping roller
31 intake auger of 30
32 intake auger of 29
33 transverse conveyor
34 auger flight
35 auger flight
36 guide frame member
37 header trough
38 front snapping plate
39 rear snapping plate
40 snapping gap
41 adjustment device
42 lower cover
43 deflector
44 snapping gap
45 snapping gap of 24 or 26
46 deflector
47 driving element
48 tooth root
49 tooth flank
50 end face
51 bevel
52 corn stalk
53 contact surfaces As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A front attachment (1) for a self-propelled combine harvester for harvesting stalked crop, comprising
    a plurality of intake conveyor mechanisms (5, 6, 7, 8 and 9), which are arranged side by side and each comprise grooved conveyor wheels (10, 11, 12, 13) that rotate about a substantially vertical rotational axis, and
    snapping units (21, 22, 27, 28) are located downstream of the intake conveyor mechanisms (5, 6, 7, 8, 9) in the direction of crop flow, and comprise snapping rollers (29, 30) extending horizontally and transversely to the direction of travel, and
    a transverse conveyor (33) is equipped with opposing auger sections (34, 35), via which harvested fruits of the stalked crop are drawn together in the center of the front attachment (1) and fed from there to a feed rake (2),
    wherein the grooved conveyor wheels of the individual intake conveyor mechanisms comprise, on the outer circumference, radially extending driving elements (47), which engage via sections into guide channels (17, 18, 23, 24) formed by a lower cover (14) and upper covers (15, 16) of the grooved conveyor wheels (10, 11, 12, 13) to pick up and convey plant stalks,
    wherein the guide channels (17, 18, 23, 24) are oriented substantially in the direction of travel in the inlet region and, in the outlet region, in the direction of a snapping gap (40, 44, 45) formed between the snapping rollers (29, 30), and
    wherein the guide channels (17, 18, 23, 24) are equipped with end sections (19, 20, 25, 26), which guide the stalked crop in the direction of the center of the attachment.

2. The front attachment according to claim 1, wherein a central intake conveyor mechanism (5) is disposed in the center of the front attachment (1) and equipped with guide channels (17 and 18) extending on both sides, end sections (19, 20) of which guide the stalked crop into the snapping unit oriented in the direction of the center of the front attachment (1) or in the conveyance direction of the transverse conveyor (33), and wherein the snapping units (21, 22) assigned to the central intake conveyor mechanism (5) are disposed in the region of the central intake conveyor mechanism (5) facing away from the direction of travel.

3. The front attachment according to claim 2, wherein in addition to the central intake conveyor mechanism (5), all inner and outer intake conveyor mechanisms (6, 7, 8, 9) are equipped with guide channels (23, 24), end sections (25, 26) of which are oriented in the direction of the center of the front attachment (1) or in the conveyance direction of the transverse conveyor (33) and lead into snapping units (27, 26), which are located spatially behind the particular inner and outer intake conveyor mechanism (6, 7, 8, 9).

4. The front attachment according to claim 2, wherein the central intake conveyor mechanism (5) comprises four grooved conveyor wheels (10, 11 and 12, 13), which rotate in opposite directions in pairs and which have rotational axes located on an isosceles trapezoid with respect to one another, and wherein one short leg of the trapezoid extends in the direction of travel and the long leg of which extends in the direction of the transverse conveyor (33).

5. The front attachment according to claim 2, wherein two pair of snapping rollers (29, 30) are assigned to the central intake conveyor mechanism (5), wherein a rear snapping roller (30) of the two pair of snapping rollers, as viewed in the direction of travel, is axially extended and comprises, in a region of the axial extension, an intake auger (31) with an outer jacket, where the intake auger (31) engages by way of a portion of the outer jacket into the end section (19, 20) of the guide channel (17, 18).

6. The front attachment according to claim 1, wherein the lower cover (14) is formed as one piece with a front snapping plate (38) of the snapping unit (21, 22, 27, 28).

7. The front attachment according to claim 6, wherein the front snapping plate (38), together with a rear snapping plate (39), delimits a snapping gap (40), which extends above the snapping rollers (29, 30) and wherein a further snapping gap (44) is located opposite the snapping gap (40).

8. The front attachment according to claim 7, wherein a deflector (43) having a tip extending in the direction of the transverse conveyor is disposed between the two-snapping gaps (40, 44), are formed behind a central intake conveyor mechanism (5) of the plurality of intake conveyor mechanisms (5, 6, 7, 8 and 9).

9. The front attachment according to claim 8, wherein a supporting rail for the central intake conveyor mechanism (5) is disposed underneath the deflector (43).

10. The front attachment according to claim 8, wherein the deflector (43) is formed at a cover of the grooved conveyor wheels (10, 11, 12, 13).

11. The front attachment according to claim 7, wherein the transverse conveyor (33) extends radially beyond the snapping gap (40, 44), and wherein the rear snapping plate (39) forms a part of a trough (37) of the front attachment (1).

12. The front attachment according to claim 7, wherein the rear snapping plate (39) is equipped with an axially acting adjustment device (41) for adjusting a width of the snapping gap (40, 44).

13. The front attachment according to claim 3, wherein the inner intake conveyor mechanisms (6, 7), which are disposed on both sides of the central intake conveyor mechanism (5), have a rhomboidal outer contour, have mirror symmetry with respect to a longitudinal central plane of the front attachment (1) and are arrangeable side by side.

14. The front attachment according to claim 13, wherein the inner intake conveyor mechanisms (6, 7) each comprise three grooved conveyor wheels (10, 11, 12, 13), and wherein two grooved conveyor wheels (10, 11) engage in the inlet region of the particular adjacent guide channels (23, 24) and rotate in opposite directions, while a third grooved conveyor wheel (12, 13) engages in the end section (25, 26) of the guide channel (23, 24).

15. The front attachment according to claim 2, wherein the snapping rollers (29, 30) assigned to inner intake conveyor mechanisms (6, 7) of the plurality of intake conveyor mechanisms (5, 6, 7, 8 and 9) have a greater overall axial length than the snapping rollers (29, 30) that interact with the central intake conveyor mechanism (5).

16. The front attachment according to claim 3, wherein a deflector (46) that extends in the direction of the transverse conveyor (33) is provided at the end of a snapping gap (45) that is assigned to one of the inner intake conveyor mechanisms (6, 7).

17. The front attachment according to claim 2, wherein the grooved conveyor wheels are equipped with driving elements (47) in the form of teeth, which teeth have a radius $R_1$ or $R_2$ at the tooth flanks (49) and a tooth root located therebetween.

18. The front attachment according to claim 2, wherein tooth flanks (49), which are oriented in the conveyance direction, of teeth of the grooved conveyor wheels (10, 11, 12, 13) extend at a slant with respect to a longitudinal central axis of the grooved conveyor wheels (10, 11, 12, 13).

19. The front attachment according to claim 2, wherein tooth flanks (49) oriented in the conveyance direction of teeth of the grooved conveyor wheels (10, 11, 12, 13) are wider than the remaining wall thickness.

20. The front attachment according to claim 2, wherein tooth flanks (49) oriented in the conveyance direction of teeth of at least one the grooved conveyor wheels (10, 11, 12, 13) are equipped with a transition radius or a chamfer (51) at a particular transition into an end face (50) of the grooved conveyor wheel (10, 11, 12, 13).

21. The front attachment according to claim 17, wherein the radii $R_1$ and $R_2$ are matched to a standard stalk diameter of corn or sunflower plants, respectively.

* * * * *